United States Patent [19]
Bowers, Jr. et al.

[11] Patent Number: 6,140,385
[45] Date of Patent: Oct. 31, 2000

[54] PHOTOACTIVE COMPOUNDS FOR USE WITH NARROW WAVELENGTH BAND ULTRAVIOLET (UV) CURING SYSTEMS

[75] Inventors: Joseph Stanton Bowers, Jr., Mobile, Ala.; Rajamani Nagarajan, Ocean Springs; Charles Uriah Pittman, Jr., Starkville, both of Miss.; E. Sonny Jönsson, Stockholm, Sweden

[73] Assignee: First Chemical Corporation, Pascagoula, Miss.

[21] Appl. No.: 09/164,233

[22] Filed: Sep. 30, 1998

Related U.S. Application Data

[62] Division of application No. 08/858,268, May 19, 1997.
[60] Provisional application No. 60/017,127, May 20, 1996.

[51] Int. Cl.$^7$ ................................ C08F 2/48; C08F 4/00; C08F 20/20
[52] U.S. Cl. ................................ 522/37; 522/46; 522/48; 522/49; 522/50; 522/53; 522/57; 522/63; 522/65; 522/68; 522/142; 522/2
[58] Field of Search .................................. 522/53, 50, 48, 522/57, 63, 65, 68, 49, 46, 37, 142, 2

[56] References Cited

U.S. PATENT DOCUMENTS

| | | |
|---|---|---|
| 3,366,691 | 1/1968 | Keller . |
| 3,595,900 | 7/1971 | Loudas et al. . |
| 3,833,658 | 9/1974 | Avar et al. . |
| 4,007,209 | 2/1977 | Hickmann et al. . |
| 4,043,887 | 8/1977 | Pacifici et al. . |
| 4,080,382 | 3/1978 | Pacifici et al. . |
| 4,199,420 | 4/1980 | Photis . |
| 4,374,984 | 2/1983 | Eichler et al. . |
| 4,518,788 | 5/1985 | Crivello . |
| 4,529,490 | 7/1985 | Crivello et al. . |
| 4,577,034 | 3/1986 | Durvasula . |
| 4,584,260 | 4/1986 | Iwasaki et al. ...................... 430/288.1 |
| 4,602,097 | 7/1986 | Curtis . |
| 4,661,434 | 4/1987 | Iwasaki et al. ...................... 430/281.1 |
| 4,666,951 | 5/1987 | Onishi et al. . |
| 4,691,059 | 9/1987 | Mitra et al. . |
| 4,714,726 | 12/1987 | Ketley . |
| 4,767,797 | 8/1988 | Ai et al. ...................... 522/8 |
| 4,843,179 | 6/1989 | Jansons et al. . |
| 4,975,471 | 12/1990 | Hayase et al. . |
| 5,310,862 | 5/1994 | Nomura et al. ...................... 528/353 |
| 5,468,904 | 11/1995 | Osawa et al. . |
| 5,504,391 | 4/1996 | Turner et al. . |
| 5,573,889 | 11/1996 | Hofmann et al. ...................... 430/269 |
| 5,686,503 | 11/1997 | Nohr et al. ...................... 522/36 |

FOREIGN PATENT DOCUMENTS

| | | |
|---|---|---|
| 0 150 891 | 8/1985 | European Pat. Off. . |
| 2 138 875 | 1/1973 | France . |
| 2617160 | 12/1988 | France . |
| 2 075 506 | 11/1981 | United Kingdom . |

*Primary Examiner*—Susan W. Berman
*Attorney, Agent, or Firm*—Alston & Bird LLP

[57] ABSTRACT

Novel substituted diaryl ketones, photopolymerization compositions including the compounds, and methods using the same are disclosed. Polymerization of compositions which include the compounds of the invention may be activated by irradiating the composition with ultraviolet light using conventional techniques and radiation sources to give greatly improved cure speeds. The compounds of the invention also show a significantly elevated level of reactivity at a narrow wavelength band, with a peak emission wavelength at or near 308 nm. Because of the increased level of activity, the photoinitiator can be used in considerably lower amounts.

41 Claims, 5 Drawing Sheets

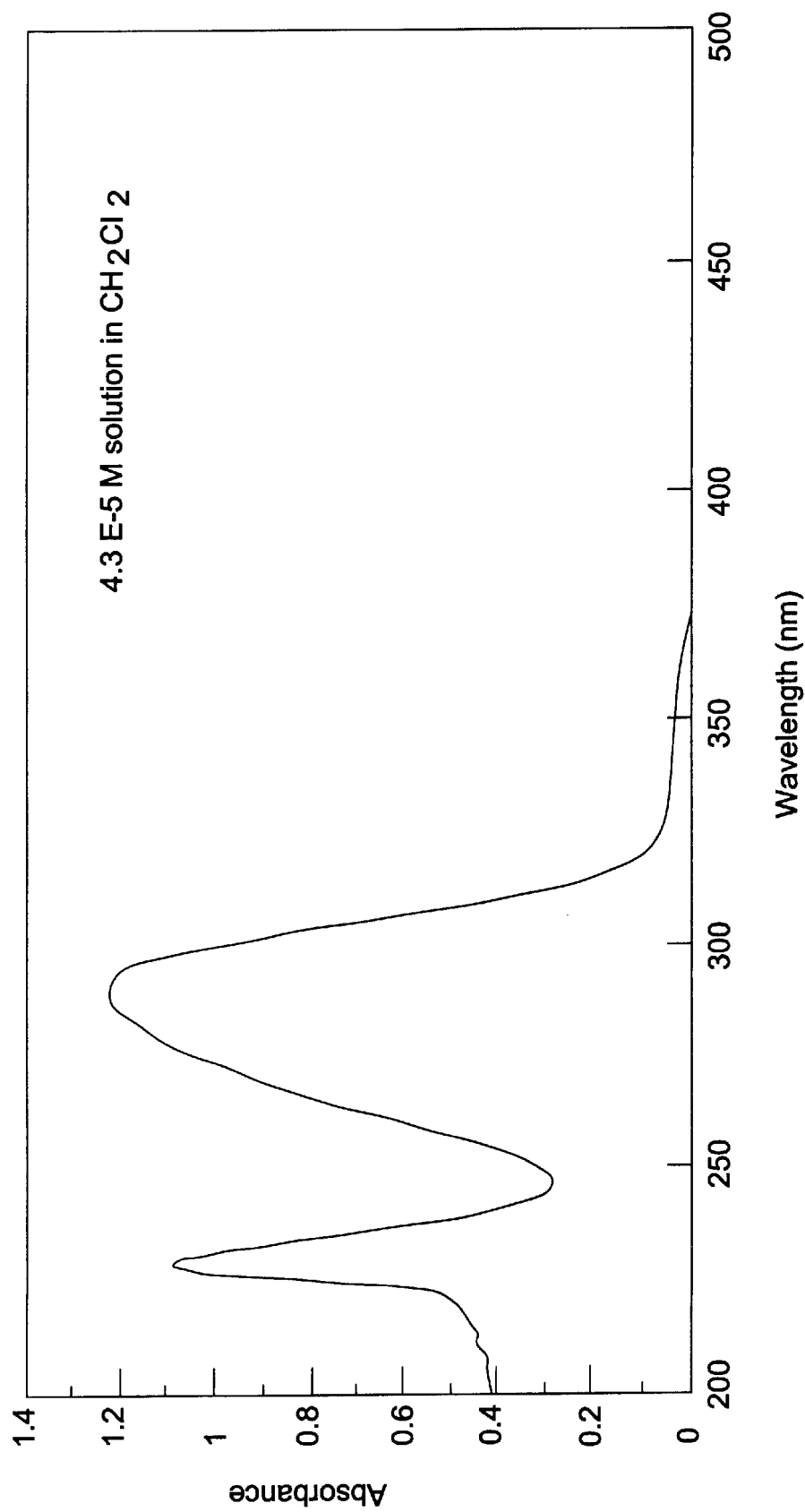

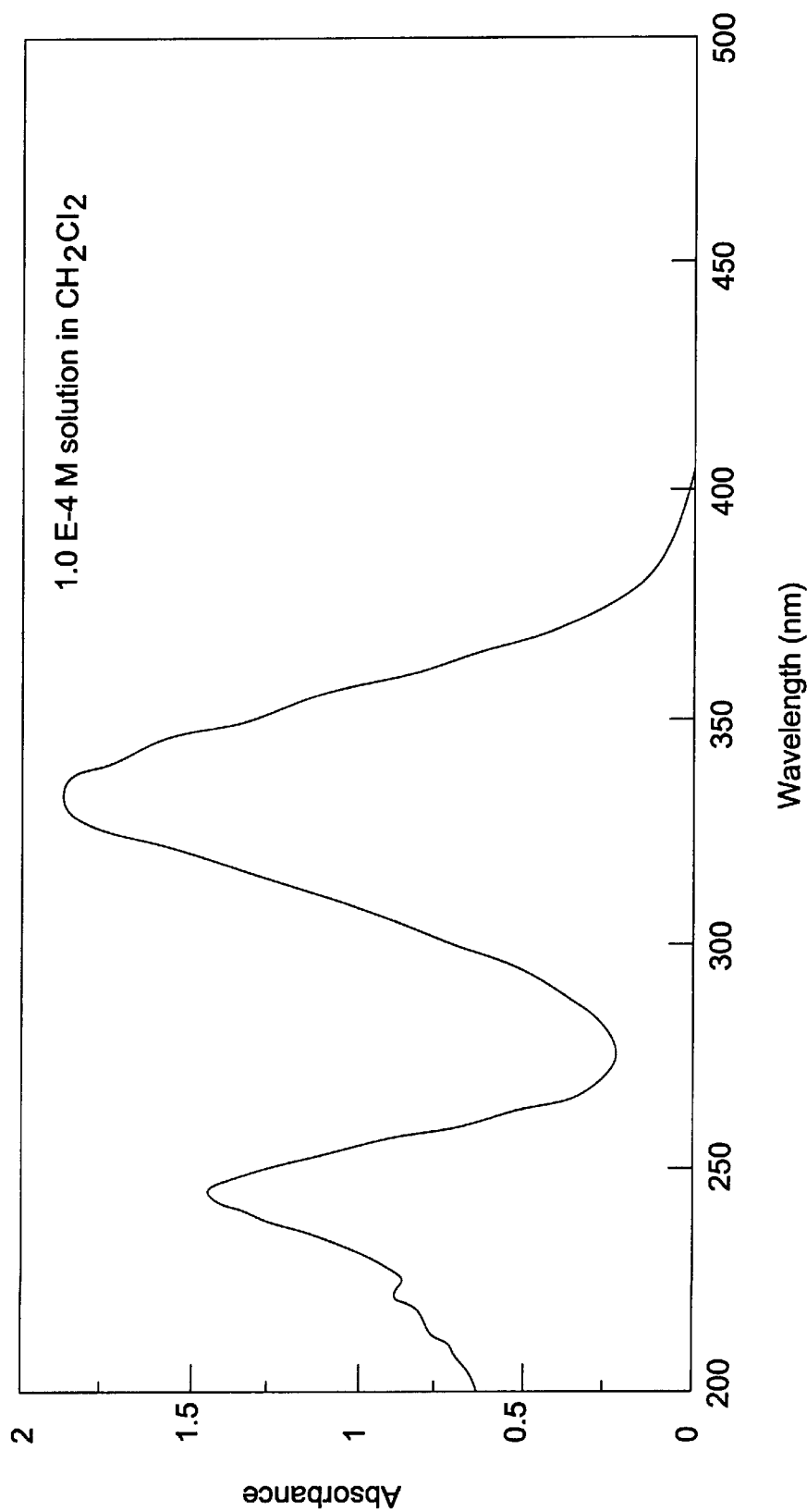

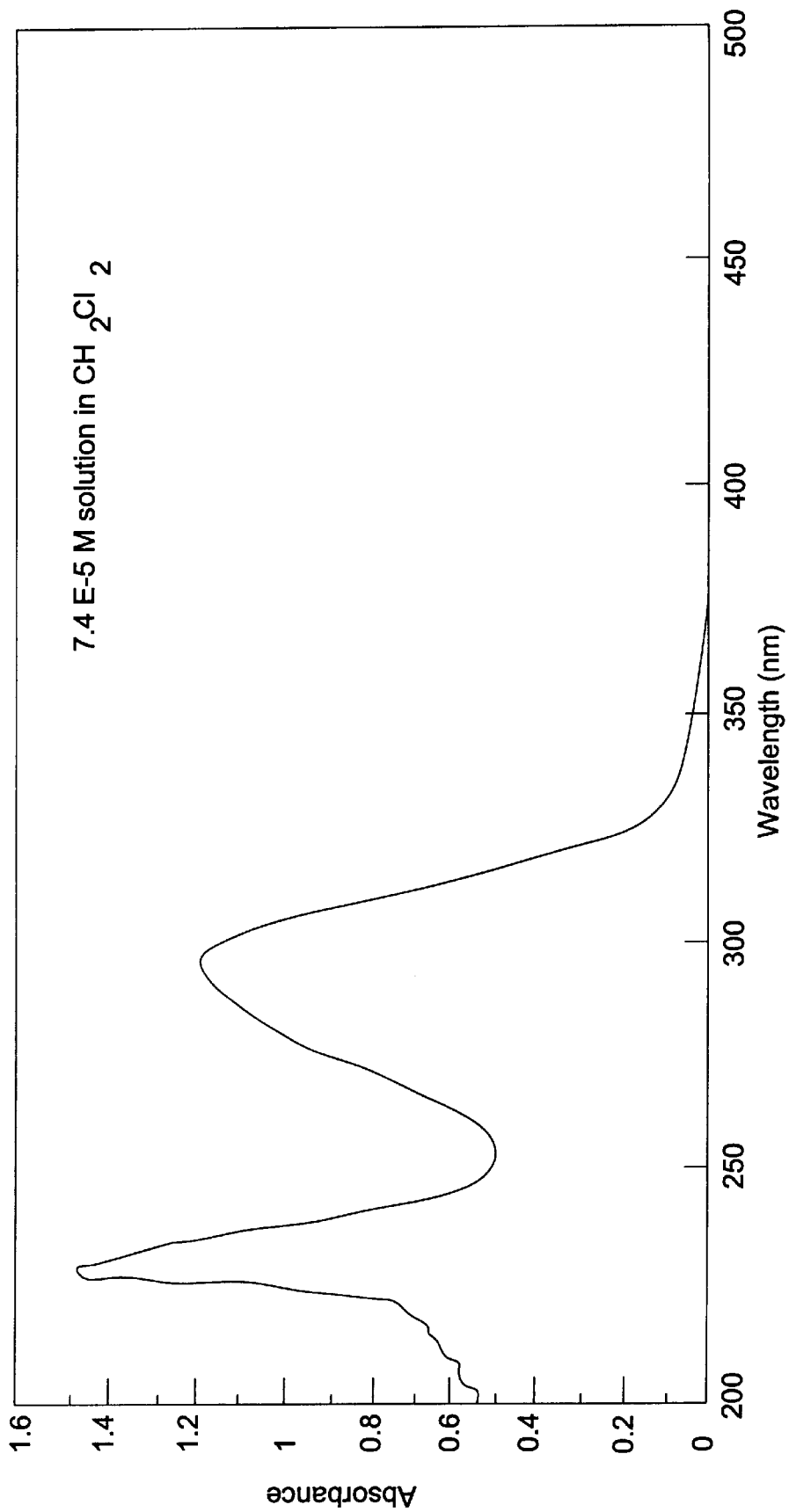

PHOTOACTIVE COMPOUNDS FOR USE WITH NARROW WAVELENGTH BAND ULTRAVIOLET (UV) CURING SYSTEMS

CROSS-REFERENCE TO RELATED APPLICATIONS

This Application is a Divisional of Application Ser. No. 08/858,268, filed May 19, 1997.

This application is related to commonly owned copending Provisional Application Ser. No. 60/017,127, filed May 20, 1996, and claims the benefit of its earlier filing date under 35 U.S.C. 119(e).

FIELD OF THE INVENTION

This invention relates generally to novel photoactive compounds and methods for using and making the same. More particularly, this invention relates to substituted diaryl ketones and methods of using the same in photoactivatable polymerization systems.

BACKGROUND OF THE INVENTION

Ethylenically unsaturated compounds, and in particular acrylate derivatives, can be polymerized by irradiation with ultraviolet light of wavelength between 200 and 450 nanometers (nm) in the presence of a bimolecular photoinitiating system. Typically, the photoinitiating system includes (1) a diaryl ketone photoinitiator and (2) a coinitiator or synergist, that is, a molecule which serves as a hydrogen atom donor. The coinitiators or synergists are typically alcohols, tertiary amines or ethers which have available hydrogens attached to a carbon adjacent to a heteroatom.

Examples of commercially available diaryl ketone photoinitiators useful in bimolecular photoinitiator systems include benzophenone, 2,4-dimethylbenzophenone, isopropylthioxanthone, and 2,4-diethylthioxanthone. The UV absorption spectrum for these individual photoinitiators, however, do not match-up efficiently with the UV emission spectra of the standard commercially available mercury vapor bulbs.

Thus, commercially viable UV curing processes can require a relatively large amount of initiator and synergist incorporated into the formulation. This can lead to cured articles which contain high levels of residual photoinitiator and synergist, which in turn can result in decreased light fastness and lower resistance to oxidative degradation. In addition, the residual photoinitiator and synergist can be extracted or leach out of the cured article or migrate to the surface of the article. Many times the physical properties of the article are degraded by the presence of the residual photoinitiator and synergist.

SUMMARY OF THE INVENTION

The present invention provides novel substituted diaryl ketones useful for photopolymerizing ethylenically unsaturated compounds. The novel compounds of the invention are particularly useful for photopolymerizing acrylate derivatives by irradiation with ultraviolet light of wavelength between 200 and 450 nm in the presence of a coinitiator or synergist. The present invention also provides photopolymerizable systems which include the novel diaryl ketone compounds of the invention as a component thereof, as well as methods for using the compounds of the invention in photopolymerization systems.

BRIEF DESCRIPTION OF THE DRAWINGS

Some of the features and advantages of the invention having been described, others will become apparent from the detailed description which follows, and from the accompanying drawings, in which:

FIG. 3 illustrates the UV absorption spectrum of 4,4'-bis (phenoxy)benzophenone;

FIG. 4 illustrates the UV absorption spectrum of 4-(N-morpholino)benzophenone; and FIG. 5 illustrates the UV absorption spectrum of 4,4'-bis (2,4-di-tert-amylphenoxy)benzophenone.

DETAILED DESCRIPTION OF THE INVENTION

Figure 1:
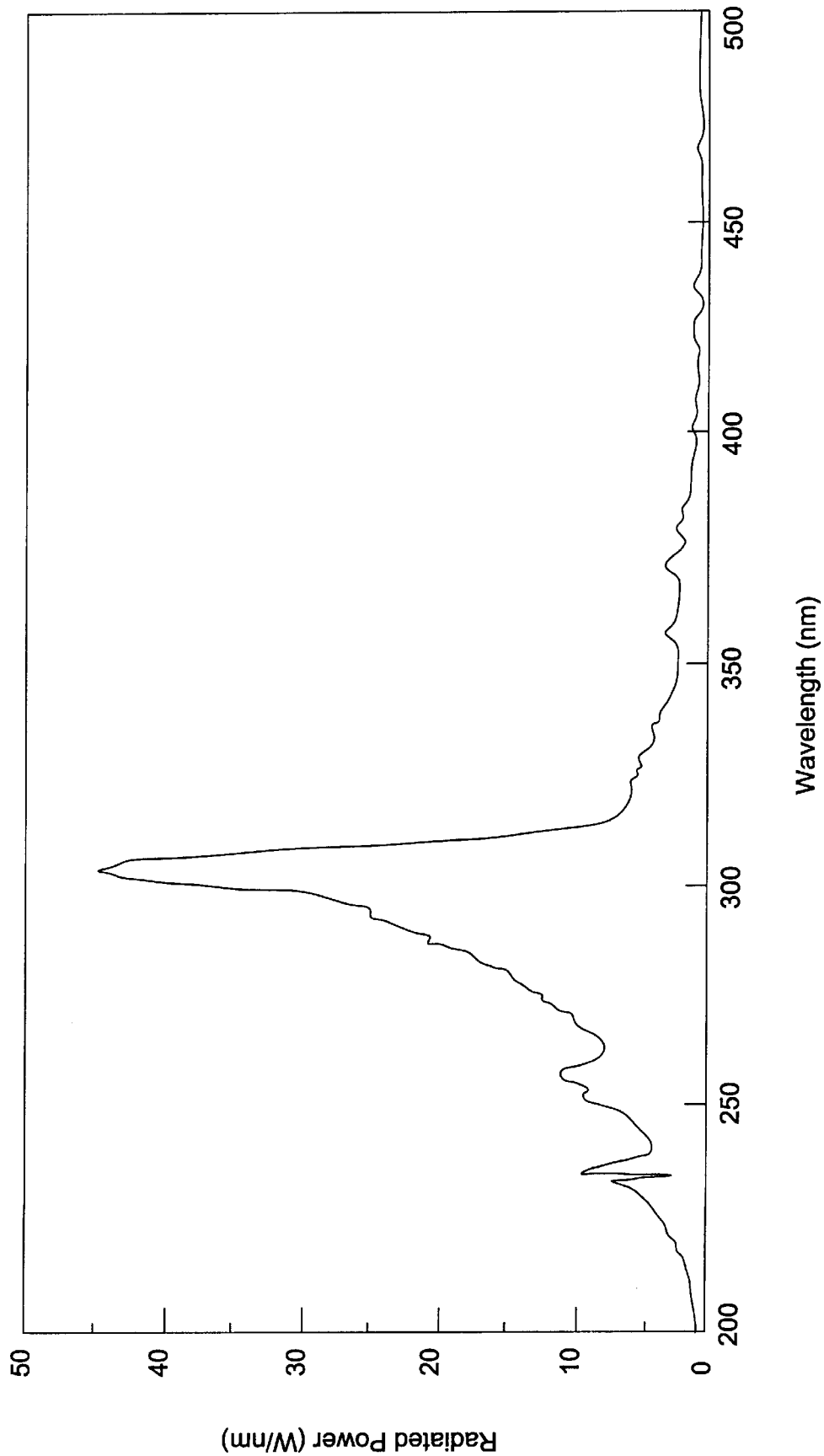
FIG. 1 illustrates the ultraviolet (UV) emission spectrum of an excimer lamp as described in U.S. Pat. No. 5,504,391.

Preferred diaryl ketones of the invention are appropriately substituted to possess UV spectra with significant absorption bands between 250 and 350 nanometers (nm), and more preferably between 290 and 325 nm. The novel compounds of the invention include substituted diaryl compounds according to Formula (I) below:

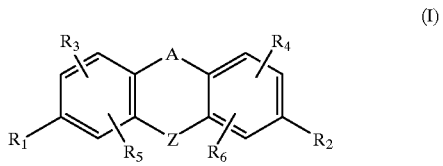

(I)

wherein:

A is —CO— or —CO—CO—;

Z is (H,H), —CH$_2$—, —S—, —O—, —CO—, —NR$_9$—, or a bond bridging the two aromatic rings, i.e.,

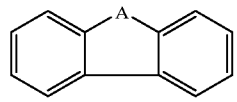

each R$_1$ and R$_2$ is independently selected from the group consisting of H,

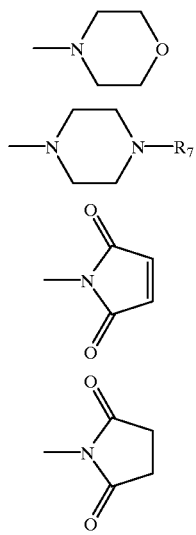

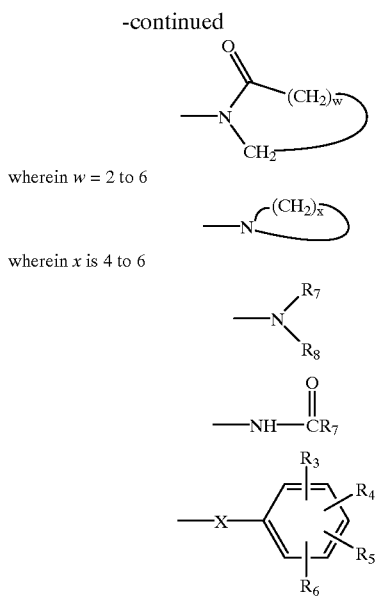

wherein w = 2 to 6 wherein x is 4 to 6 and

X—R$_7$;

X is O or S;

each R$_3$, R$_4$, R$_5$, and R$_6$ is independently selected from the group consisting of —H, —Cl, —Br, —NO$_2$, —CN, —OH, C1 to C8 alkyl, C6 to C8 aryl, C7 to C24 alkylaryl or arylalkyl, C1 to C8 alkoxy, C6 to C18 aryloxy, C7 to C24 alkylaryloxy or arylalkoxy, C1 to C8 alkylthioether, —COOH, and —COOR$_7$; and each R$_7$, R$_8$ and R$_9$ is independently selected from the group consisting of C1 to C8 alkyl and C7 to C24 alkylaryl or arylalkyl.

Exemplary compounds in accordance with Formula I include but are not limited to 4,4,'-bis(4-isopropylphenoxy)benzophenone, 4,4'-bis(phenoxy)benzophenone, 4-(N-morpholino)benzophenone, and 4,4,'-bis(2,4-di-t-amylphenoxy)benzophenone.

Generally the compounds of Formula (I) can be prepared using techniques known in the art for preparing 4,4'-disubstituted diaryl ketones, and in particular 4,4'-diphenoxybenzophenone, as well as other substituted diphenoxy-benzophenones. These processes are known in the open literature as well as the patent literature. For example, Crochemore (FR 2,617,160) teaches reacting diphenylether with substituted phenoxybenzoic acids in liquid HF at about 50°. Towle (EP 262,919) teaches reacting diphenylether and a substituted phenoxybenzoyl chloride in a chlorinated solvent in the presence of a Friedel-Crafts catalyst and a protic controlling agent to obtain better isomeric purity. Keller (U.S. Pat. No. 3,366,691) teaches the preparation of diphenoxybenzophenones by reacting diphenyl ethers with AlCl$_3$ and phosgene at about 80° C. Janson et al. (U.S. Pat. No. 4,843,179) teaches reacting diphenyl ether with carbon dioxide under pressure at about 148° C. in the presence of a promoting agent such as phosphoryl chloride. Each of the above Crochemore, Towle, Keller, and Janson references are incorporated in their entirety by reference.

In another embodiment of the invention, photopolymerizable compositions are provided which include a compound of Formula (I) above as a photoinitiator. As used herein, and as will be appreciated by the skilled artisan, the term photopolymerizable composition refers to compositions which harden or cure upon exposure to radiation.

Generally the compositions of the invention include ethylenically unsaturated compounds, including monomers, oligomers, polymers, prepolymers, resinous materials, optionally dispersed or dissolved in a suitable solvent that is copolymerizable therewith, and mixtures thereof, which are photopolymerizable when exposed to a source of UV radiation. As will be appreciated by the skilled artisan, the photopolymerizable compounds can be monofunctional, or can include two or more terminal polymerizable ethylenically unsaturated groupings per molecule.

Exemplary photopolymerizable compounds or precursors include, but are not limited to, reactive vinyl monomers, including acrylic monomers, such as acrylic and methacrylic acids, and their amides, esters, salts and corresponding nitriles. Suitable vinyl monomers include, but are not limited to, methyl acrylate, ethyl acrylate, n- or tert-butylacrylate, isooctyl acrylate, methyl methacrylate, ethylmethacrylate, 2-ethylhexyl methacrylate, butylacrylate, isobutyl methacrylate, the corresponding hydroxy acrylates, i.e., hydroxy ethylacrylate, hydroxy propylacrylate, hydroxy ethylhexyl methacrylate, glycol acrylates, i.e., ethylene glycol dimethacrylate, hexamethylene glycol dimethacrylate, the allyl acrylates, i.e., allyl methacrylate, diallyl methacrylate, the epoxy acrylates, i.e., glycidyl methacrylate, and the aminoplast acrylates, i.e., melamine acrylate. Others such as vinyl acetate, vinyl and vinylidene halides and amides, i.e., methacrylamide, acrylamide, diacetone acrylamide, butadiene, styrene, vinyl toluene, and the like are also included. Prepolymers include acrylated epoxides, polyesters and polyurethanes, and are typically combined with a suitable monomer for viscosity control. The photopolymerizable compounds may be polymerized to form homopolymers or copolymerized with various other monomers.

The photoinitiator is present in the photopolymerizable composition in an amount sufficient to initiate polymerization of photopolymerizable compounds therein upon exposure to ultraviolet radiation. One advantage of the compounds of the invention is the decreased amounts required to initiate polymerization in comparison to conventional photoinitiators. The composition can include about 0.001 to about 10 percent by weight photoinitiator, preferably about 0.005 to about 0.10, based on the total weight of the photopolymerizable compounds.

It can be advantageous to also include as a component of the compositions a coinitiator or synergist, that is, a molecule which serves as a hydrogen atom donor. Coinitiators or synergists are known in the art, and are typically alcohols, tertiary amines or ethers which have available hydrogens attached to a carbon adjacent to a heteroatom. Such co-initiators are typically present in an amount of about 0.2 to about 25 percent by weight based on the total weight of the composition. Suitable compounds include triethanolamine, methyl-diethanolamine (MDEA), ethyldiethanolamine and esters of dimethylamino benzoic acid. These compounds behave as co-initiators or accelerators for the primary photoinitiators and can increase the efficiency and speed of the polymerization process.

In addition, the photopolymerizable compositions may contain polymerization inhibitors, fillers, ultraviolet absorbers and organic peroxides.

The photopolymerizable compositions can be applied or deposited on a surface of a substrate using conventional techniques and apparatus. The composition can be applied as a substantially continuous film; alternatively, the composition can be applied in a discontinuous pattern. Usually the compositions of the invention are fluid at ordinary operating temperatures (between ambient and up to about 60° C.).

The thickness of the deposited composition can vary, depending upon the desired thickness of the resultant cured product. Advantageously, the composition is applied to the substrate surface in an amount sufficient to provide a cured coating having a thickness between about 1 micron and about 5 mils.

Typically, the substrate is coated with the uncured photopolymerizable composition and passed under a ultraviolet providing light beam by a conveyer moving at predetermined speeds. The substrate to be coated can be, for example, metal, wood, mineral, glass, paper, plastic, fabric, ceramic, and the like.

The active energy beams used in accordance with the present invention may be visible light or ultraviolet light or may contain in their spectra both visible and ultraviolet light. The polymerization may be activated by irradiating the composition with ultraviolet light using any of the techniques known in the art for providing ultraviolet radiation, i.e., in the range of 200 nm and 450 nm ultraviolet radiation. The radiation may be natural or artificial, monochromatic or polychromatic, incoherent or coherent and should be sufficiently intense to activate the photoinitiators of the invention and thus the polymerization. Conventional radiation sources include fluorescent lamps, mercury, metal additive and arc lamps. Coherent light sources are the pulsed nitrogen, xenon, argon ion- and ionized neon lasers whose emissions fall within or overlap the ultraviolet or visible absorption bands of the compounds of the invention.

As noted above, preferably the diaryl ketones of the invention are appropriately substituted to possess UV spectra with significant absorption bands between 250 and 350 nm and in particular between 290 and 325 nm. Accordingly, the compounds can be irradiated with a narrow wavelength band, high pressure fill UV curing lamp known as an excimer lamp with spectral emphasis in the 250 to 350 nm range, and in particular with its peak emission wavelength at or near 308 nm, as described in U.S. Pat. No. 5,504,391, the entire disclosure of which is hereby incorporated in its entirety. The compounds of Formula (I) show a significantly elevated level of reactivity at these wavelengths. Because of the increased level of activity the photoinitiator can be used in considerably lower amounts.

When polymerized by exposure to UV radiation, the compositions can give a substantially tack-free product which is durable for ordinary handling. The compositions are useful in any of the types of applications known in the art for photopolymerizations, including as a binder for solids to yield a cured product in the nature of a paint, varnish, enamel, lacquer, stain or ink. The compositions are particularly useful in the production of photopolymerizable surface coatings in printing processes, such as lithographic printing, screen printing, and the like.

The present invention will be further illustrated by the following non-limiting examples.

EXAMPLE 1

Synthesis of 4,4,'-Dibromobenzophenone 4,4'-Dibromobenzophenone, a tuned photoinitiator precursor, can be prepared by the ambient temperature reaction of p-bromobenzoyl chloride with bromobenzene, catalyzed by anhydrous aluminum chloride. This preparation is described by W. J. Leigh et al., Can. J. Chem., 58, 1980, pp. 2537–2549.

EXAMPLE 2

Synthesis of 3,6-Dibromoanthrone 3,6-Dibromoanthrone, a tuned photoinitiator precursor, can be prepared by first producing 2,7-dibromoanthraquinone by the direct bromination of anthraquinone with elemental bromine under pressure at about 160° C. as described by Diehl, Chem. Ber, 11, 1878, p181. The dibromoanthraquinone is then reduced to the 3,6-dibromoanthrone with aluminum metal and sulfuric acid as described by R. Biehl, et al., J. Amer. Chem. Soc., 99(13), 1977, pp.4278–4286.

EXAMPLE 3

Synthesis of 2,7-Dibromoxanthone 2,7-Dibromoxanthone, a tuned photoinitiator precursor, can be prepared by the direct bromination of xanthone using elemental bromine with a trace of iodine as catalyst in, acetic acid at about 100° C. This preparation is described by P. R. J. Gaffney et al., J. Chem. Soc., Perkin Trans. 1, 1991(6), pp.1355–1360.

The 2,7-Dibromoxanthone can also be prepared by the phosgenation of 4,4'-dibromo-diphenyl ether using aluminum chloride as catalyst. This process is described in U.S. Pat. No. 2,776,299.

EXAMPLE 4

Synthesis of 2-Aminothioxanthone

Thiosalicyclic acid (6 g.) was dissolved in 200 g. of 98% sulfuric acid and cooled to 5° C. for 16 hours and then quenched into ice water. The precipitate was stirred with 5% aqueous caustic for 2 hours, filtered, and washed with water. The precipitate was then stirred with 50/50 acetonitrile/acetone to remove unreacted acetanilide. The resulting product was hydrolyzed in 70% sulfuric acid at 80–105° C. for 8 hours to give after neutralization, washing and drying 2-aminothioxanthone, a tuned photoinitiator precursor, mp 227–229° C. Structure was confirmed by IR, NMR, C-13 NMR and MS.

EXAMPLE 5

Synthesis of 2,Morpholinothioxanthone

2-Aminothioxanthone (4.9 g.), anhydrous potassium carbonate (4.5 g.) and di(ethylene-glycol) diethyl ether (150 ml) were heated to reflux (180° C.) and 5.2 g. of 2-bromoethyl ether was added. The reaction was held at reflux for 24 hours, filtered hot and the solvent removed under vacuum. The residue was recrystallized from acetone to give 2-morpholinothioxanthone, mp 166–167° C. Structure was confirmed by IR, NMR, C-13 NMR and MS.

EXAMPLE 6

Synthesis of Michler's Ketone Type Compounds

Michler's Ketone type compound such as p,p'-dicyclobutylaminobenzophenone can be prepared by reacting about 4.3 molar equivalents of N-phenylcyclobutylamine with one molar equivalent of phosgene at under 24° C. to form the 4-cyclobutylamino-benzoyl chloride. The addition of the $ZnCl_2$ completes the reaction to produce the desired compound. This process is described in U.S. Pat. No. 2,882,472.

EXAMPLE 7

Synthesis of 4,4'-bis(4-Isopropylphenoxy) benzophenone

To a solution of 4-isopropylphenol (20.4 g.) in 30 ml of dimethylformamide was added slowly a slurry of sodium hydride, 60% in mineral oil (6.0 g.) in 150 ml of dimethylformamide. When the reaction was complete, 8.5 g. of 4,4'-dibromobenzophenone and 1.0 g. dendritic copper powder were added and the reaction mixture heated to reflux and held at reflux for 24 hours. The solvent was removed under vacuum and the residue poured into ice-water. The crude product was recrystallized from ethanol to give the desired compound, mp 104–105° C. Structure was confirmed by IR, NMR, C-13 NMR and MS.

EXAMPLE 8

Synthesis of 4,4'-bis[2,4-di(1,1-Dimethylpropyl) phenoxy]benzophenone

The same process as example 7 was followed except that di-tert-amylphenol was used in place of 4-isopropylphenol. After recrystallization from ethanol the desired compound was obtained, mp 54–56° C. Structure was confirmed by IR, NMR, C-13 NMR and MS.

EXAMPLE 9

Synthesis of 4-Morpholinobenzophenone

4-Morpholinobenzophenone was found commercially available from Aldrich Chemical Co.

EXAMPLE 10

Synthesis of 4,4'-Diphenoxybenzophenone

Diphenoxybenzophenone can be prepared by the aluminum chloride catalyzed reaction between diphenyl ether and phosgene over about 3 hours at 80° C. and 45 psig pressure. The resulting product has a mp 146–147° C. This process is described in U.S. Pat. No. 3,366,691. We prepared 4,4'-diphenoxybenzophenone by the same procedure used in Example 7 to prepare 4,4'-bis(4-isopropylphenoxy) benzophenone, except that phenol was used in place of 4-isopropyl-phenol. The mp of the product compound agreed with the literature and the structure was confirmed by IR, NMR, C-13 NMR and MS.

EXAMPLE 11

Synthesis of 3,6-Diphenoxyanthrone Derivatives

Starting with 3,6-dibromoanthrone, diphenoxyanthrone derivatives could be prepared by one skilled in the art using the same process as Example 7, except that 3,6-dibromoanthrone is used in place of 4,4'-dibromobenzophenone and the appropriate phenol is used in place of 4-isopropylphenol.

EXAMPLE 12

A resin blend was prepared from 501 grams polyester polyol derivative sold under the name EB80 from UCB Radcure, 120 grams glyceryl propoxy triacrylate sold under the name OTA-480, and 250 grams tripropyleneglycol diacrylate. This blend was used for all photopolymerizations. Methyldiethanolamine, MDEA, was added to a portion of the blend to provide 1.5 weight percent MDEA. The photoinitiators were added in the amounts shown in tables 1 and 2, and the mixtures were applied to provide 2 mil films on paper panels. The paper panels were passed under an excimer lamp which has a peak emission wavelength at or near 308 nm. For comparison the paper panels were also passed under a medium pressure mercury lamp. Both lamps were set for 400 watts per inch. Cure speeds were determined as the maximum belt speed at which the film passed the thumb twist test, and are given in the following tables.

TABLE 1

| Initiator | Cure Speed (Feet per minute) | Concentration of photoinitiator for Medium Pressure Mercury Lamp (Wt. %) | Concentration of photoinitiator for Excimer Lamp (Wt. %) |
| --- | --- | --- | --- |
| Benzophenone | 150 | 1.5 | — |
| 4,4'-Bis(4-isopropylphenoxy)-benzophenone | 270 | 0.04 | 0.01 |
| 4,4'-Bis(phenoxy)-benzophenone | 425 | 0.053 | 0.013 |
| 4-(N-Morpholino)-benzophenone | 325 | 0.02 | 0.007 |
| 4,4'-Bis(2,4-di-t-amylphenoxy)-benzophenone | 325 | 0.056 | 0.011 |

TABLE 2

| Initiator | Concentration of photoinitiator (Wt. %) | Cure Speed for Medium Pressure Mercury Lamp (Feet per minute) | Cure Speed for Excimer Lamp (Feet per minute) |
| --- | --- | --- | --- |
| Benzophenone | 1.5 | 150 | 290 |
| 4,4'-Bis(4-isopropylphenoxy)-benzophenone | 0.04 | 270 | >590 |
| 4,4'-Bis(phenoxy)-benzophenone | 0.053 | 425 | >590 |
| 4-(N-Morpholino)-benzophenone | 0.02 | 325 | >590 |
| 4,4'-Bis(2,4-di-t-amylphenoxy)-benzophenone | 0.055 | 325 | >590 |

The results in Table 1 show that when the compounds of the invention are used with an excimer lamp versus a medium pressure mercury lamp that only about one-fourth of the amount of photoinitiator is required to give equivalent cure speeds.

The results in Table 2 show that when the same concentration of photoinitiator is used with both an excimer and a medium pressure mercury lamp that the excimer lamp provides greatly increased cure speeds.

Both tables show that the compounds of the invention provide cure speeds much higher than does benzophenone.

Figure 2:
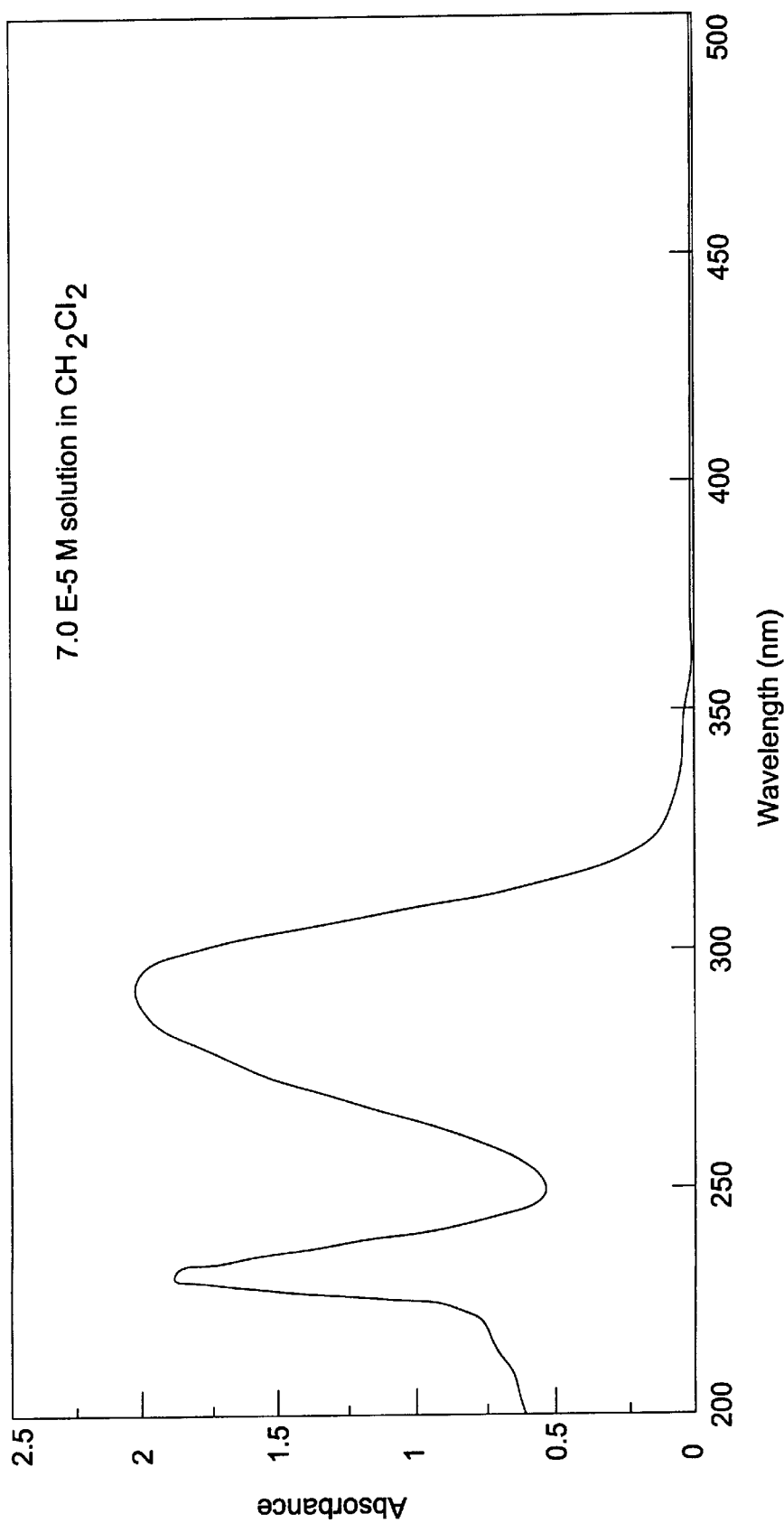
FIG. 2 illustrates the UV absorption spectrum of 4,4'-bis (4-isopropylphenoxy)benzophenone.

UV Spectra are provided for the excimer lamp, and for the four compounds of the invention used in the example, 4,4'-bis(4-isopropylphenoxy)benzophenone, 4,4'-bis(phenoxy)benzophenone, 4-(N-morpholino)benzophenone, and 4,4'-bis(2,4-di-t-amylphenoxy)benzophenone in FIGS. 1, 2, 3, 4, and 5, respectively.

The foregoing examples are illustrative of the present invention and are not to be construed as limiting thereof. The invention is defined by the following claims, with equivalents of the claims to be included therein.

That which is claimed is:

1. A photopolymerizable composition comprising a photopolymerizable compound comprising at least one ethylenically unsaturated double bond and a photoinitiator having the Formula (I)

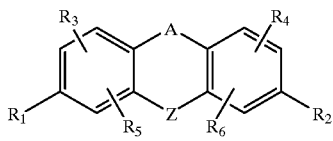

wherein:
A is —CO— or —CO—CO—;
Z is (H,H), —CH$_2$—, —S—, —O—, —CO—, —NR$_9$—, or a bond bridging the two aromatic rings,
each R$_1$ and R$_2$ is independently selected from the group consisting of H, with the proviso that both R$_1$ and R$_2$ are not H;

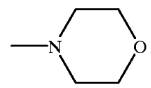

with the proviso that Z is not (H,H) when at least one of R$_1$ or R$_2$ is morpholino,

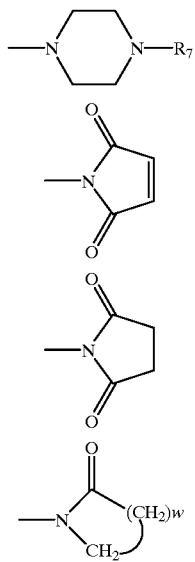

wherein $w$ = 2 to 6 wherein $x$ is 4 to 5

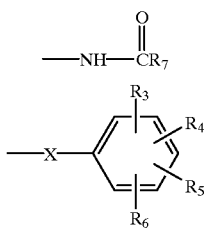

with the proviso that when Z is —S— and X is oxygen, then at least one of R$_1$ and R$_2$ is not phenoxy or toluyloxy and with the proviso that when Z is —S— and X is sulfur, then at least one of R$_1$ or R$_2$ is not thiophenyl or substituted thiophenyl; and X—R$_7$ with the proviso that R$_7$ is not arylalkyl;

X is O or S;

each R$_3$, R$_4$, R$_5$, and R$_6$ is independently selected from the group consisting of —H, —Cl, —Br, —NO$_2$, —CN, —OH, C1 to C8 alkyl, C6 to C8 aryl, C7 to C24 alkylaryl or arylalkyl, C1 to C8 alkoxy, C6 to C18 aryloxy, C7 to C24 alkylaryloxy or arylalkoxy, C1 to C8 alkylthioether, —COOH, and —COOR$_7$; and each R$_7$ is independently selected from the group consisting of C1 to C8 alkyl and C7 to C24 alkylaryl or arylalkyl.

2. The composition of claim 1, wherein at least one of R$_1$ and R$_2$ is

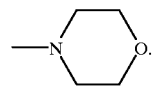

3. The composition of claim 1, wherein at least one of R$_1$ and R$_2$ is

4. The composition of claim 1, wherein at least one of R$_1$ and R$_2$ is

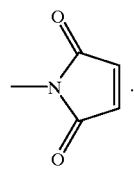

5. The composition of claim 1, wherein at least one of R$_1$ and R$_2$ is

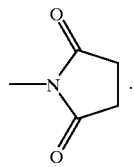

6. The composition of claim 1, wherein at least one of R$_1$ and R$_2$ is

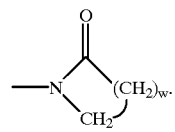

7. The composition of claim 1, wherein at least one of R$_1$ and R$_2$ is

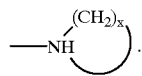

8. The composition of claim 1, wherein at least one of $R_1$ and $R_2$ is

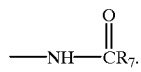

9. The composition of claim 1, wherein at least one of $R_1$ and $R_2$ is

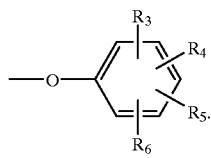

10. The composition of claim 9, wherein at least one of $R_3$, $R_4$, $R_5$ and $R_6$ is branched alkyl.

11. The composition of claim 1, wherein at least one of $R_1$ and $R_2$ is

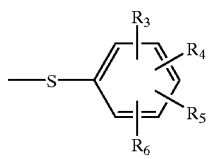

and wherein Z is (H,H).

12. The composition of claim 1, wherein at least one of $R_1$ and $R_2$ is X—$R_7$.

13. The composition of claim 1, wherein A is —CO—.

14. The composition of claim 1, wherein Z is (H,H).

15. The composition of claim 1, wherein $R_1$ and $R_2$ are the same.

16. The composition of claim 15, wherein $R_1$ and $R_2$ are each

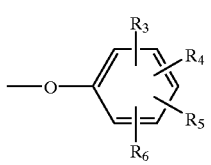

wherein at least one of $R_3$, $R_4$, $R_5$ or $R_6$ is branched alkyl.

17. The composition of claim 16, wherein said compound is selected from the group consisting of 4,4'-bis(4-isopropylphenoxy)benzophenone, 4,4'-bis(2,4-di-t-amylphenoxy)benzophenone, and mixtures thereof.

18. A method of polymerizing a polymerizable compound comprising at least one ethylenically unsaturated double bond, comprising exposing said compound to ultraviolet radiation in the presence of a photoinitiator compound having the Formula (I)

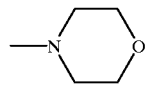

(I)

wherein
A is —CO— or —CO—CO—;
Z is (H,H), —$CH_2$—, —S—, —O—, —CO—, —$NR_9$—, or a bond bridging the two aromatic rings,
each $R_1$ and $R_2$ is independently selected from the group consisting of H, with the proviso that both $R_1$ and $R_2$ are not H;

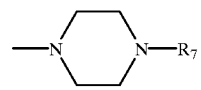

with the proviso that Z is not (H,H) when at least one of $R_1$ or $R_2$ is morpholino,

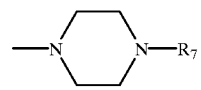

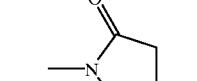

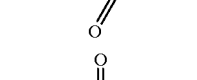

wherein $w$ = 2 to 6

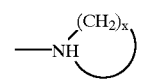

wherein $x$ is 4 to 5

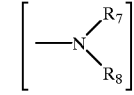

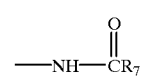

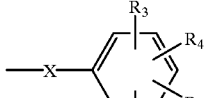

with the proviso that when Z is —S— and X is oxygen, then at least one of $R_1$ and $R_2$ is not phenoxy or toluyloxy and with the proviso that when Z is —S— and X is sulfur, then at least one of $R_1$ or $R_2$ is not thiophenyl or substituted thiophenyl; and
X—$R_7$ with the proviso that $R_7$ is not arylalkyl;
X is O or S;

each $R_3$, $R_4$, $R_5$, and $R_6$ is independently selected from the group consisting of —H, —Cl, —Br, —NO$_2$, —CN, —OH, C1 to C8 alkyl, C6 to C8 aryl, C7 to C24 alkylaryl or alkylaryl or arylalkyl, C1 to C8 alkoxy, C6 to C18 aryloxy, C7 to C24 alkylaryloxy or arylalkoxy, C1 to C8 alkylthioether, —COOH, and —COOR$_7$; and each $R_7$ is independently selected from the group consisting of C1 to C8 alkyl and C7 to C24 alkylaryl or arylalkyl.

19. The method of claim 18, wherein said exposing step comprises exposing said composition to radiation using a narrow wavelength band excimer lamp having spectral emphasis in a wavelength band of about 250 to about 350 nanometers (nm).

20. The method of claim 18, wherein said exposing step comprises exposing said composition to radiation using a narrow wavelength band excimer lamp having spectral emphasis in a wavelength band of about 290 to about 325 nm.

21. The method of claim 18, wherein said exposing step comprises exposing said composition to radiation using a narrow wavelength band excimer lamp having spectral emphasis in a wavelength band of about 308 nm.

22. The method of claim 18, wherein at least one of $R_1$ and $R_2$ is

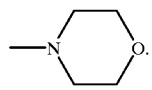

23. The method of claim 18, wherein at least one of $R_1$ and $R_2$ is

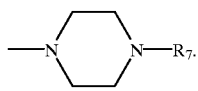

24. The method of claim 18, wherein at least one of $R_1$ and $R_2$ is

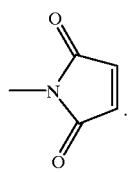

25. The method of claim 18, wherein at least one of $R_1$ and $R_2$ is

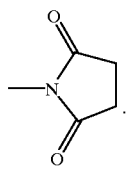

26. The method of claim 18, wherein at least one of $R_1$ and $R_2$ is

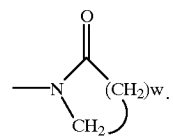

27. The method of claim 18, wherein at least one of $R_1$ and $R_2$ is

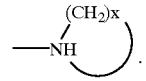

28. The method of claim 18, wherein at least one of $R_1$ and $R_2$ is

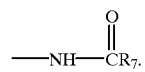

29. The method of claim 18, wherein at least one of $R_1$ and $R_2$ is

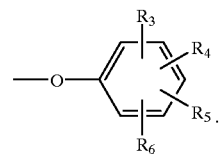

30. The method of claim 29, wherein at least one of $R_3$, $R_4$, $R_5$ and $R_6$ is branched alkyl.

31. The method of claim 18, wherein at least one of $R_1$ and $R_2$ is

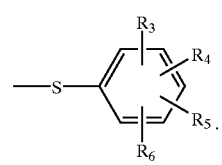

32. The method of claim 18, wherein at least one of $R_1$ and $R_2$ is X—$R_7$.

33. The method of claim 18, wherein A is —CO—.

34. The method of claim 18, wherein Z is (H,H).

35. The method of claim 18, wherein $R_1$ and $R_2$ are the same.

36. The method of claim 35, wherein $R_1$ and $R_2$ are each

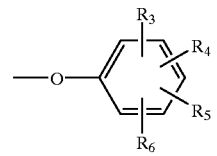

wherein at least one of $R_3$, $R_4$, $R_5$ or $R_6$ is branched alkyl.

37. The method of claim 36, wherein said compound is selected from the group consisting of 4,4'-bis(4-isopropylphenoxy)benzophenone, and 4,4'-bis(2,4-di-t-amylphenoxy)benzophenone, and mixture thereof.

38. A method of polymerizing a polymerizable compound comprising at least one ethylenically unsaturated double bond, comprising exposing said compound to ultraviolet radiation using a narrow wavelength band excimer lamp emitting a narrow radiation wavelength band between about 250 to about 350 nanometers (nm) in the presence of a photoinitiator compound having the Formula (I)

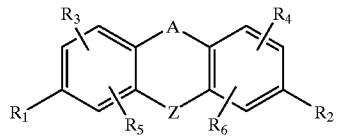

wherein:
A is —CO— or —CO—CO—;
Z is (H,H), —CH$_2$—, —S—, —O—, —CO—, —NR$_9$—, or a bond bridging the two aromatic rings,
each R$_1$ and R$_2$ is independently selected from the group consisting of H, with the proviso that both R$_1$ and R$_2$ are not H;

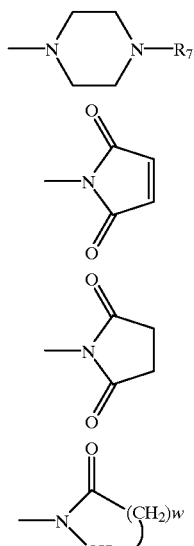

wherein $w$ = 2 to 6

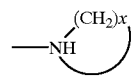

wherein $x$ is 4 to 5

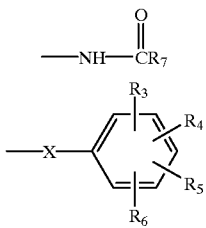

and
X—R$_7$;
X is oxygen or sulfur;
each R$_3$, R$_4$, R$_5$, and R$_6$ is independently selected from the group consisting of —H, —Cl, —Br, —NO$_2$, —CN, —OH, C1 to C8 alkyl, C6 to C8 aryl, C7 C24 alkylaryl or arylalkyl, C1 to C8 alkoxy, C6 to C18 aryloxy, C7 to C24 alkylaryloxy or arylalkoxy, C1 to C8 alkylthioether, —COOH, and —COOR$_7$; and each R$_7$ and R$_8$ is independently selected from the group consisting of C1 to C8 alkyl and C7 to C24 alkylaryl or arylalkyl.

39. The method of claim 38, wherein said compound is selected from the group consisting of 4,4'-bis(4-isopropylphenoxy)benzophenone, and 4,4'-bis(2,4-di-t-amylphenoxy)benzophenone, and mixtures thereof.

40. A photopolymerizable composition comprising a photopolymerizable compound comprising at least one ethylenically unsaturated double bond and a photoinitiator having the Formula (I)

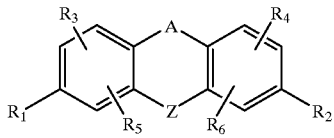

wherein:
A is —CO—;
Z is (H, H);
each R$_1$ and R$_2$ is

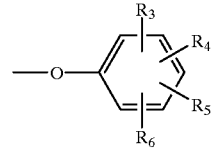

wherein each R$_3$, R$_4$, R$_5$, and R$_6$ is independently selected from the group consisting of —H, —Cl, —Br, —NO$_2$, —CN, —OH, C1 to C8 alkyl, C6 to C8 aryl, C7 to C24 alkylaryl or arylalkyl, C1 to C8 alkoxy, C6 to C18 aryloxy, C7 to C24 alkylaryloxy or arylalkoxy, C1 to C8 alkylthioether, —COOH, and —COOR$_7$, with the proviso that at least one R$_3$, R$_4$, R$_5$, and R$_6$ of the phenoxy group is branched alkyl.

41. A method of polymerizing a polymerizable compound comprising at least one ethylenically unsaturated double bond, comprising exposing said compound to ultraviolet radiation in the presence of a photoinitiator compound having the Formula (I)

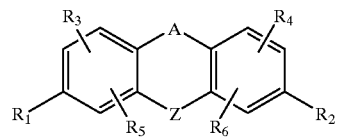

wherein:
A is —CO—;
Z is (H, H);
each R$_1$ and R$_2$ is

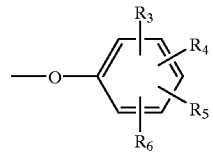

wherein each R$_3$, R$_4$, R$_5$, and R$_6$ is independently selected from the group consisting of —H, —Cl, —Br, —NO$_2$, —CN, —OH, C1 to C8 alkyl, C6 to C8 aryl, C7 to C24 alkylaryl or alylalkyl, C1 to C8 alkoxy, C6 to C18 aryloxy, C7 to C24 alkylaryloxy or arylalkoxy, C1 to C8 alkylthioether, —COOH, and —COOR$_7$, with the proviso that at least one $R_3$, $R_4$, $R_5$, and $R_6$ of the phenoxy group is branched alkyl.

* * * * *